(12) United States Patent
Dennis

(10) Patent No.: US 7,037,307 B2
(45) Date of Patent: May 2, 2006

(54) AUTOMATICALLY DEFORMING SURGICAL SNARE

(76) Inventor: William G. Dennis, c/o 11222-4 St. Johns Industrial Pkwy., Jacksonville, FL (US) 32246

(*) Notice: Subject to any disclaimer, the term of this patent is extended or adjusted under 35 U.S.C. 154(b) by 32 days.

(21) Appl. No.: 10/837,940

(22) Filed: May 3, 2004

(65) Prior Publication Data

US 2005/0043743 A1 Feb. 24, 2005

Related U.S. Application Data

(63) Continuation-in-part of application No. 10/006,042, filed on Dec. 7, 2001, now Pat. No. 6,730,097.

(51) Int. Cl.
*A61B 18/14* (2006.01)

(52) U.S. Cl. .................... 606/47; 606/113; 606/110

(58) Field of Classification Search ............. 606/41, 606/45, 47, 110–114
See application file for complete search history.

(56) References Cited

U.S. PATENT DOCUMENTS

| | | |
|---|---|---|
| 3,791,387 A | 2/1974 | Itoh |
| 4,950,273 A | 8/1990 | Briggs |
| 5,304,183 A | 4/1994 | Gourlay et al. |
| 5,730,704 A | 3/1998 | Avitall |
| 5,738,683 A | 4/1998 | Osypka |
| 5,759,187 A | 6/1998 | Nakao et al. |
| 5,800,444 A | 9/1998 | Ridinger et al. |
| 5,814,052 A | 9/1998 | Nakao et al. |
| 5,823,956 A | 10/1998 | Roth et al. |
| 5,906,620 A | 5/1999 | Nakao et al. |
| 6,071,281 A | 6/2000 | Burnside et al. |
| 6,258,101 B1 | 7/2001 | Blake, III |
| 6,299,612 B1 * | 10/2001 | Ouchi .................. 606/47 |

* cited by examiner

*Primary Examiner*—Lee Cohen
*Assistant Examiner*—Aaron Roane
(74) *Attorney, Agent, or Firm*—Hunton & Williams LLP

(57) ABSTRACT

A surgical instrument and method for facilitating the capture of objects during surgery are provided. The surgical instrument includes a flexible tube defining a cable passageway and being configured for insertion of at least portion of the flexible tube into a body cavity of a patient. The surgical instrument further includes flexible cable slidably disposed in the cable passageway. A snare loop is attached to the cable end and both are adapted so that the snare loop can be selectively retracted or extended within the cable passageway by sliding the cable proximally or distally within the cable passageway. The loop member is adapted for selectively encircling and engaging at least a portion of an object in the body cavity. The system also comprises a tether, the tether attached to the loop member at one end and to the flexible tube at the other, so that extension of the flexible cable causes the snare loop to deform in a predetermined manner.

7 Claims, 17 Drawing Sheets

AUTOMATICALLY DEFORMING SURGICAL SNARE

CROSS-REFERENCE TO RELATED APPLICATIONS

This application is a continuation-in-part of U.S. patent application Ser. No. 10/006,042 filed Dec. 7, 2001 and now issued as U.S. Pat. No. 6,730,097, the specification of which is incorporated herein by reference in its entirety.

BACKGROUND OF THE INVENTION

This invention relates generally to surgical instruments and more particularly to instruments such as snares that may be used for grasping and removing material during surgery.

During surgery, there is often a need for the collection and removal of tissue specimens such as polyps or other material from a body cavity of the patient. The removal of such tissue is often accomplished through the use of a snare device or slip-knotted suture loop that is inserted into the patient through a cannula. The snare device is generally mounted to the end of a cable slidably disposed within a flexible tube. The user of the snare device must maneuver the end of the flexible tube and cable through the body cavity, which may have a number of convolutions such as in the case of an intestinal cavity. The snare must then be maneuvered so as to surround the material to be grasped and then cinched around the material, typically using an external actuation mechanism.

The maneuverability of the snare device is generally limited to motion resulting from extension or retraction of the snare from the end of the flexible tube, extension or retraction of the flexible tube and the cable/rod and, under certain circumstances, rotation of the flexible tube and the cable/rod. This limited maneuverability can make it difficult to position the snare around the material of interest, particularly in areas where there is little room for repositioning of the tube and/or cannula.

SUMMARY OF THE INVENTION

There is accordingly a need for a surgical instrument snare with an additional manipulation capability that facilitates the maneuvering of the snare to encircle material within a body cavity of a patient.

Accordingly, an embodiment of the present invention provides a surgical instrument for facilitating the capture of objects during surgery. The surgical instrument comprises a flexible tube having a proximal tube end and a distal tube end, the flexible tube defining a cable passageway and being configured for insertion of at least a distal portion of the flexible tube into a body cavity of a patient. The surgical instrument further comprises a flexible cable having a proximal cable end and a distal cable end. At least a portion of the flexible cable is slidably disposed in the cable passageway. A snare loop having a loop member is attached to the distal cable end. The snare loop and the cable are adapted so that the snare loop can be selectively retracted within the cable passageway by sliding the flexible cable proximally relative to the cable passageway. The snare loop and the cable are also adapted so that at least a portion of the snare loop can be selectively extended from the distal tube end by sliding the flexible cable distally relative to the cable passageway. The snare loop has a longitudinal loop diameter and is adapted for selectively encircling and engaging at least a portion of an object in the body cavity. The surgical instrument also comprises a first tether having a proximal first tether end and a distal first tether end defining a tether length dimension. The distal first tether end is attached to the loop member and the proximal first tether end is attached to the flexible tube.

Other objects and advantages of the invention will be apparent to one of ordinary skill in the art upon reviewing the detailed description of the invention.

DETAILED DESCRIPTION OF THE INVENTION

The present invention provides a surgical instrument to allow a surgeon to remotely manipulate an automatically deforming snare loop and to maneuver the deformed snare loop in position around an object or tissue inside a body cavity of a patient. By "deform," it is meant that the snare loop is oriented in more than one plane.

Figure 1:
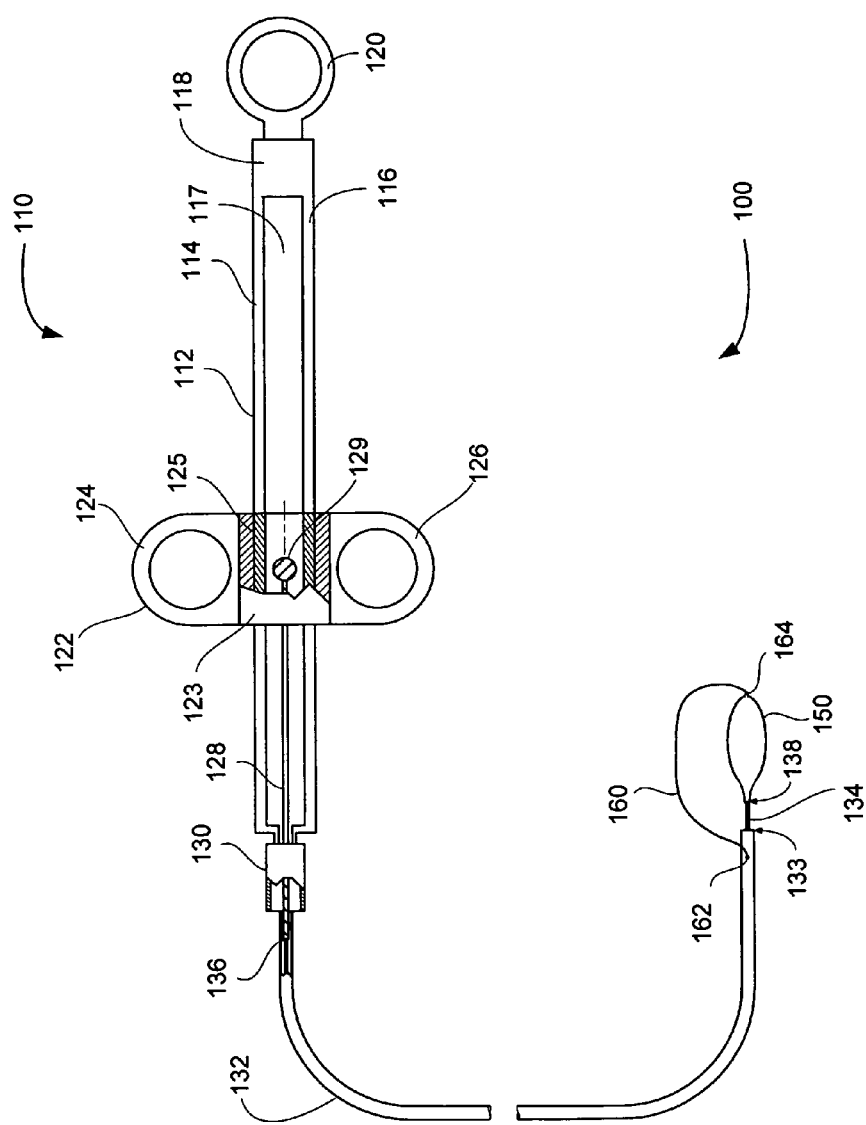
FIG. 1 is a partially sectioned view of a surgical instrument according to an embodiment of the invention.
Figure 2:
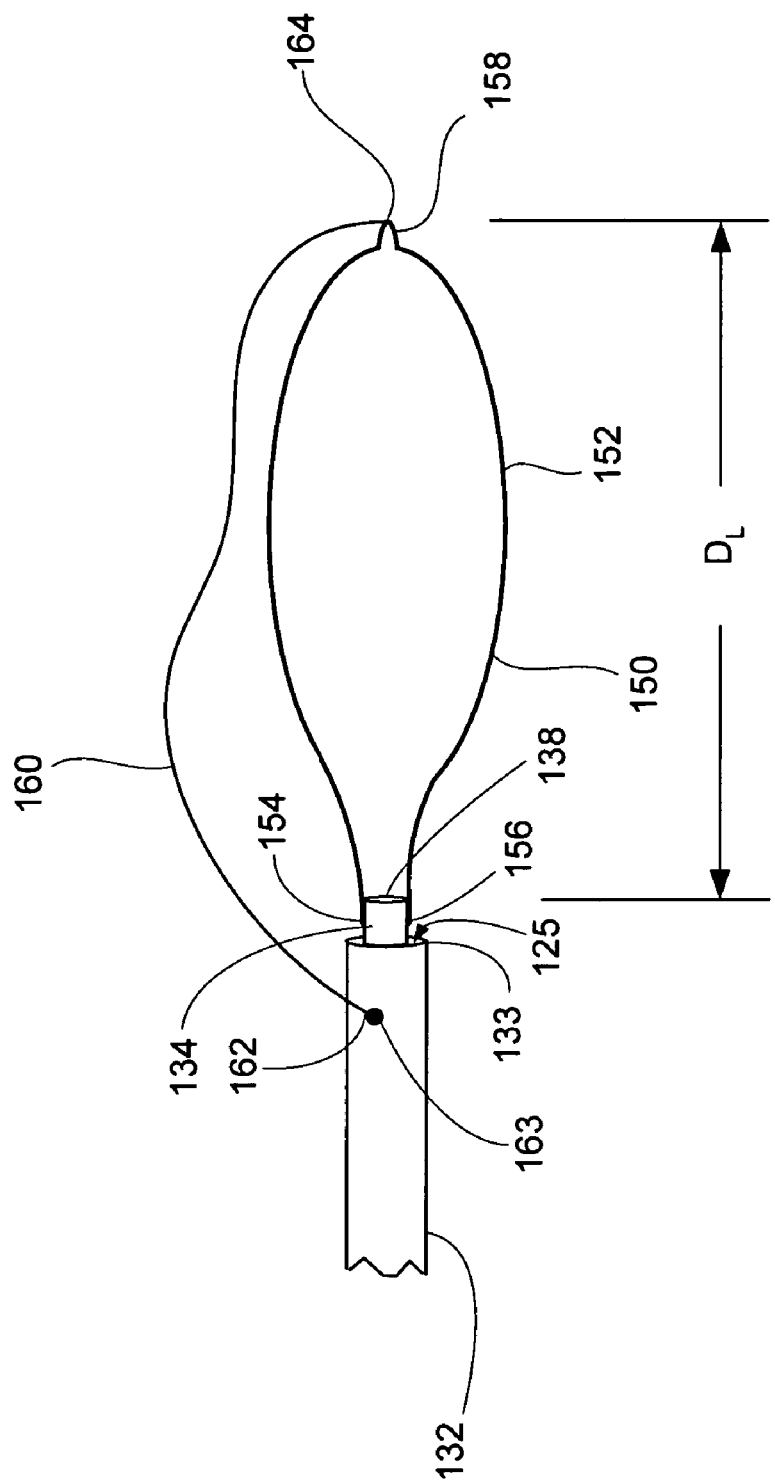
FIG. 2 is a perspective view of a snare loop of the surgical instrument illustrated in FIG. 1.

FIGS. 1 and 2 illustrate a surgical instrument 100 according to one embodiment of the invention. The surgical instrument 100 includes a snare control module 110 that is used to control the deployment and retraction of a snare loop 150 from a flexible tube 132. The snare loop 150 is formed from a resilient loop member 152. The loop member 152 has first and second ends 154, 156 that are attached to a flexible cable 134 at its distal end 138. The resilient loop member 152 may take the form of a wire, cable or band formed from metal or a resilient plastic. The resilient loop member 152 may also be a suture material attached to a biasing member or material. The resilient loop member 152 may be formed from an electrically conductive material for use as a cauterization loop. The loop member 152 may be attached to the cable 134 in any conventional manner such as bonding or welding.

The flexible cable 134 is slidably disposed within a flexible tube 132 formed from a polymer or other material suitable for use in surgical applications. The flexible tube 132 has an inside diameter sized to accommodate the flexible cable 134 and the snare loop 150. In particular, the flexible tube 132 is sized so that the snare loop 150 can be easily retracted into the distal end 133 of the flexible tube 132 when the flexible cable 134 is moved proximally relative to the flexible tube 132 and extended out of and from the flexible tube 132 when the cable is moved distally relative to the flexible tube 132.

The snare loop 150 is formed so that when freed from the flexible tube 132, it will form a substantially elliptical loop that can be used to encircle an object, although the snare loop may be formed into any geometrical shape. As the ends 154, 156 of the resilient loop member 152 are drawn into the flexible tube 132, the loop member 152 is cinched to a smaller and smaller loop. If an object is encircled by the loop member 152, the loop member 152 can be tightened around the object to secure the snare loop 150 to the object. If no object is encircled, the snare loop 150 may be drawn within the flexible tube 132.

The loop member 152 may be formed so as to include an extension 158 that extends outward from the distal end of the elliptical loop formed by the loop member 152. Such an extension can be used to facilitate the capture and retrieval of certain objects.

The snare control module 110 may be used to control the retraction and extension of the snare loop 150 from the flexible tube 132. The snare control module 110 has a generally cylindrical body 112, a control slide 122, an actuation rod 128 and a tube connector 130. The body 112 of the snare control module 110 is formed by two frame members 114, 116 and a proximal end portion 118. The frame members 114, 116 and the end portion 118 may be integrally formed into a single body structure. The frame members 114, 116 define a central frame opening 117 that runs diametrically through the body 112.

The control slide 122 has a central portion 123 having a cable passageway 125 formed therethrough. The cable passageway 125 is sized to slidably accommodate the body 112 within the cable passageway 125. This allows the control slide 122 to be reciprocated along the body 112.

The proximal end 135 of the flexible tube 132 is attached to the distal end of the body by a hollow, cylindrical connector 130. Alternatively, the tube flexible 132 may have a flange (not shown) at its proximal end 135 that can be used to hold the proximal end 135 in place within the connector 130. The connector 130 may be attached to the body 112 by internal threads configured to mate with external threads on the frame members 114, 116.

An actuation rod 128 is attached at one end to the proximal end 136 of the cable 134 and at its other end to an actuation rod pin 129 attached to the central portion 123 of the control slide 122. The actuation rod pin 129 is positioned diametrically across the cable passageway 125 within the central frame opening 117 so that it does not impede the reciprocal motion of the control slide 122. When the control slide 122 is moved toward the proximal end of the body 112, the actuation rod 128 also moves in this direction, which, in turn, moves the proximal end 136 of the cable 134 proximally relative to the flexible tube 132. When the control slide 122 is moved away from the proximal end of the body 112, the actuation rod 128 moves the proximal end 136 of the cable 134 distally relative to the flexible tube 132.

The reciprocal motion of the control slide 122 can thus be used to control the deployment of the snare loop 150 from and the retraction of the snare loop 150 into the distal tube end 133. Moving the control slide 122 distally causes the snare loop 150 to be extended from the flexible tube 132. Moving the control slide 122 proximally causes the withdrawal of the snare loop 150 toward and into the flexible tube 132.

To facilitate one hand control of the reciprocal motion of the control slide 122, finger rings 124, 126 may be attached to the central portion 123 of the control slide 122 and a thumb ring 120 may be attached to the proximal portion 118 of the body 112.

It will be understood by those having ordinary skill in the art that other mechanisms could be used in the snare control module 110 without departing from the scope and spirit of the present invention. Such mechanisms may include, for example, slide actuators without finger rings and actuators configured for use in electro-cautery.

Figure 4:
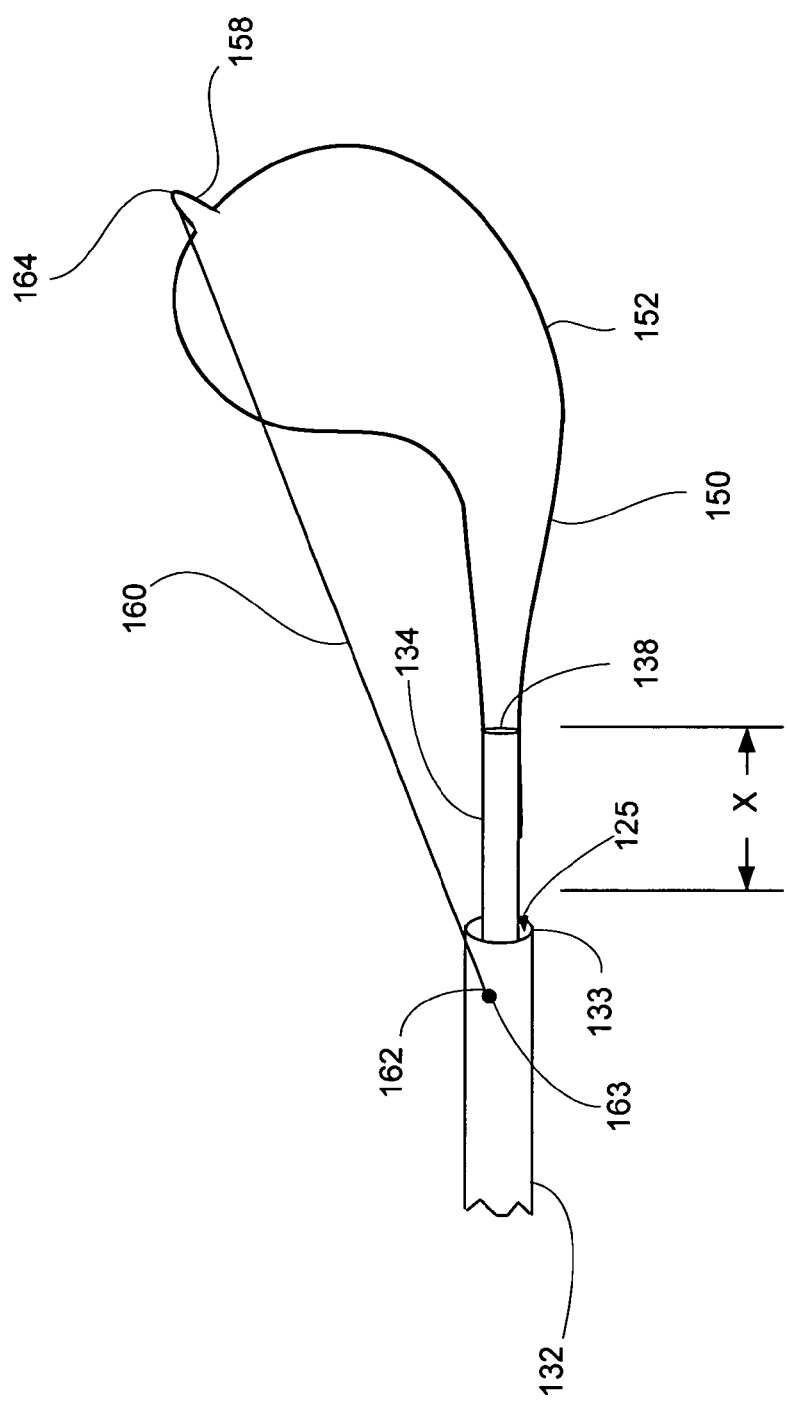
FIG. 4 is a perspective view of a snare loop of the surgical instrument illustrated in FIG. 1.

The surgical instrument 100 also includes a tether 160 that can be used to assist in maneuvering the snare loop 150. The tether 150 is attached to the flexible tube 132 and the snare loop 150 so that extension of the snare loop 150 a predetermined distance from the distal tube end 133 causes the snare loop 150 to deform from a substantially planar condition as shown in FIG. 2 to a curved three dimensional condition as shown in FIG. 4. As will be discussed, deforming the snare loop 150 in this manner serves to facilitate the positioning of the snare loop 150 for capturing body tissue such as polyps. The tether 160 of the surgical instrument 100 has a distal end 164 that is attached to the loop member 152 and a proximal end 162 that is attached to the flexible tube 132. In the illustrated embodiment the proximal tether end 162 is attached to the flexible tube 132 at an attachment point 163 near the distal tube end 133. The proximal tether end 162 may be attached to the flexible tube 132 by any suitable method such as bonding, welding or tying, and may be attached to the exterior surface of the tube 132 or to the interior surface. If attached to the interior surface of the tube 132, a portion of the tether 160 would, of course, be disposed within the cable passageway 125. The distal tether end 164 may be attached to the loop member 152 anywhere around the circumference of the snare loop 150. In the illustrated embodiment, the distal tether end 164 is attached at the distal-most point on the loop member 152. This positioning of the tether attachment is particularly useful in assisting the surgeon in maneuvering the snare loop 150 over an object such as a polyp.

The tether 160 may be formed from any thread-like structure including but not limited to thread, wire, cable and chain. The tether 160 may be formed from any suitable material including but not limited to steel or other metal, polymeric materials such as nylon, and twisted cotton or other textile materials.

The proximal tether end 162 may be attached at any point on the flexible tube 132 which is sufficient to create a tensile force on tether 160. The tether has an operative length that is useful in determining a preferred tether length. The operative length dimension of the tether 160 is defined as the distance along the tether 160 from the attachment point 163 of the proximal tether end 162 to the attachment point of the distal tether end 164 less the distance of the attachment point 163 from the distal tube end 133. When the attachment point 163 of the proximal tether end 162 is immediately adjacent the distal tube end 133, the tether length and the operative ether length are the same.

Figure 3:
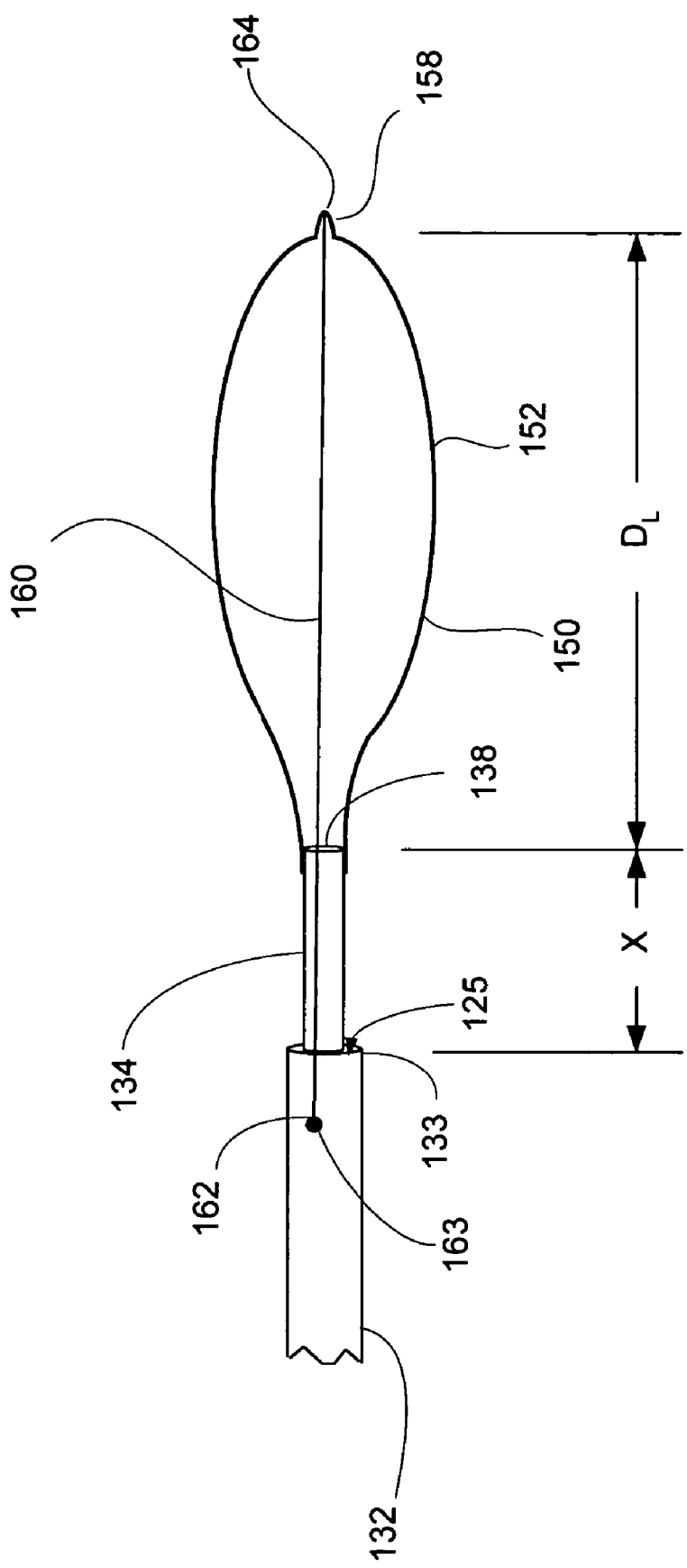
FIG. 3 is a perspective view of a snare loop of the surgical instrument illustrated in FIG. 1.

The operative tether length and the location of the tether attachment point 163 on the flexible tube 132 determine the degree to which the snare loop 15 is deformed for a given amount of extension of the snare loop 150 from the distal tube end 133. For example, if the operative tether length is greater than the longitudinal diameter DL of the snare loop 150, the snare loop 150 can be fully extended from the distal tube end 133 without deforming the snare loop 150 from its substantially planar condition (see FIG. 3). If the snare loop 150 is extended beyond a predetermined distance X (where X is the operative tether length minus DL) from the distal tube end 133, the snare loop 150 begins to deform (see FIG. 4). If, however, the operative tether length is less than the longitudinal diameter DL of the snare loop 150, the snare loop 150 will begin to deform even before it is completely extended from the distal tube end 133.

In either case, a predetermined condition wherein the snare loop 150 has adopted a desired three dimensional shape can be achieved by moving the flexible cable 134 (and thus, the snare loop 150) distally a predetermined distance relative to the flexible tube. The predetermined condition may be any degree of deformation deemed efficacious for a particular procedure.

A desirable operative tether length can be expressed in terms of tether length ratio, which may be defined as the ratio of the operative tether length divided to the longitudinal diameter DL of the snare loop 150. In instances where it is desirable for the snare loop 150 to begin to deform prior to complete deployment, it has been found that a satisfactory operative tether length ratio may be in a range from about 0.3 to about 0.7. A particularly satisfactory tether length ratio may be in a range from about 0.4 to about 0.6.

Figure 5:
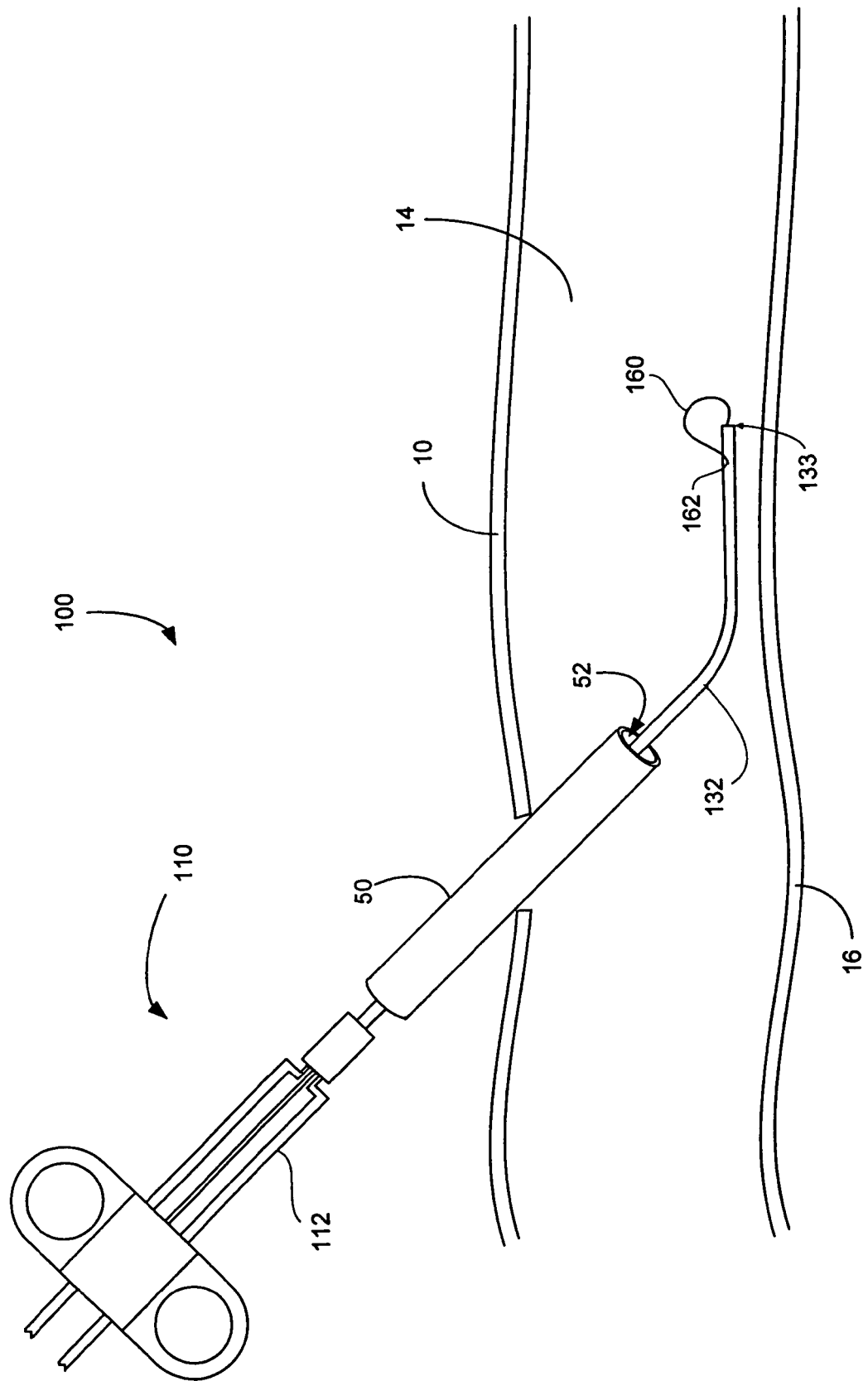
FIG. 5 is a perspective view of a surgical instrument according to the invention with a portion of the instrument inserted into a body cavity.
Figure 6:
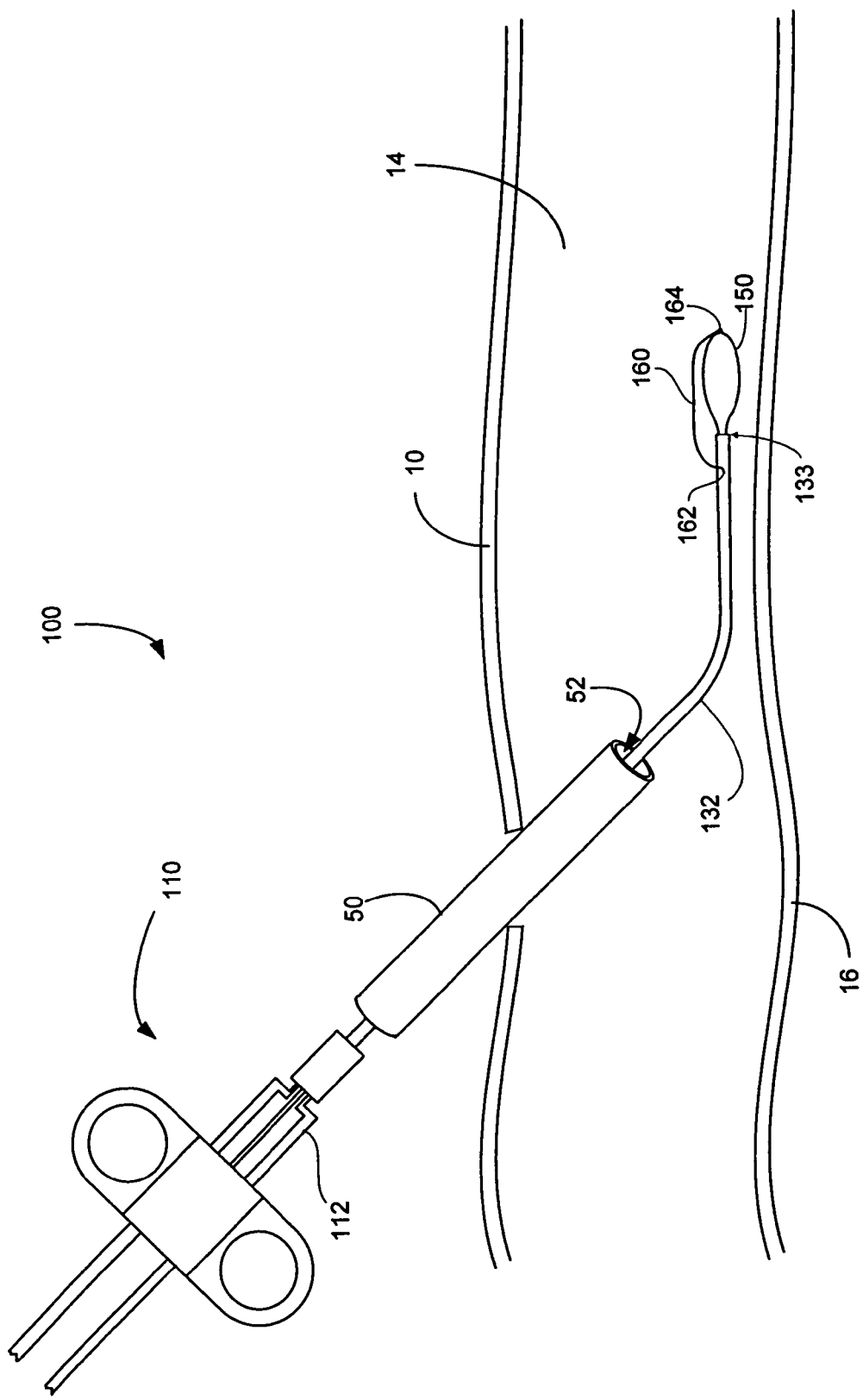
FIG. 6 is a perspective view of a surgical instrument according to the invention with a portion of the instrument inserted into a body cavity.

Turning now to FIGS. 5 and 6, the flexible tube 132 and the snare loop 150 may be introduced into a body cavity 14 through the lumen 52 of a cannula 50. The body cavity 14 is defined by first and second tissue walls 10 and 16. As shown, the cannula 50 has been inserted through an opening 12 in the first tissue layer 10. The distal end 133 of the flexible tube 132 may be passed through the cannula 50 into the cavity 14 with the snare loop 150 in a stowed position within the tube 132 as shown in FIG. 4. In this configuration, the distal tether end 164 of the tether 160, which is attached to the snare loop 150, is also withdrawn within the flexible tube 132.

The flexible tube 132 and the flexible cable 134 are formed so as to be sufficiently flexible to pass through any curves in the cavity 14 that may be encountered as the flexible tube 132 is inserted. Once the flexible tube 132 has been inserted and positioned near the area of interest, the control slide 122 of the snare control module 110 can be moved in the distal direction relative to the body 112 to cause the snare loop 150 to be extended as shown in FIG. 6. It will be understood that, depending on the relative sizes of the snare loop 150 and the cannula lumen 52, it may be possible to insert the flexible tube 132 through the cannula 50 with the snare loop 150 already partially or completely deployed. In either case, the snare loop 150 and the tether 160 may be positioned within the cavity 14 as shown in FIG. 6.

Figure 7:
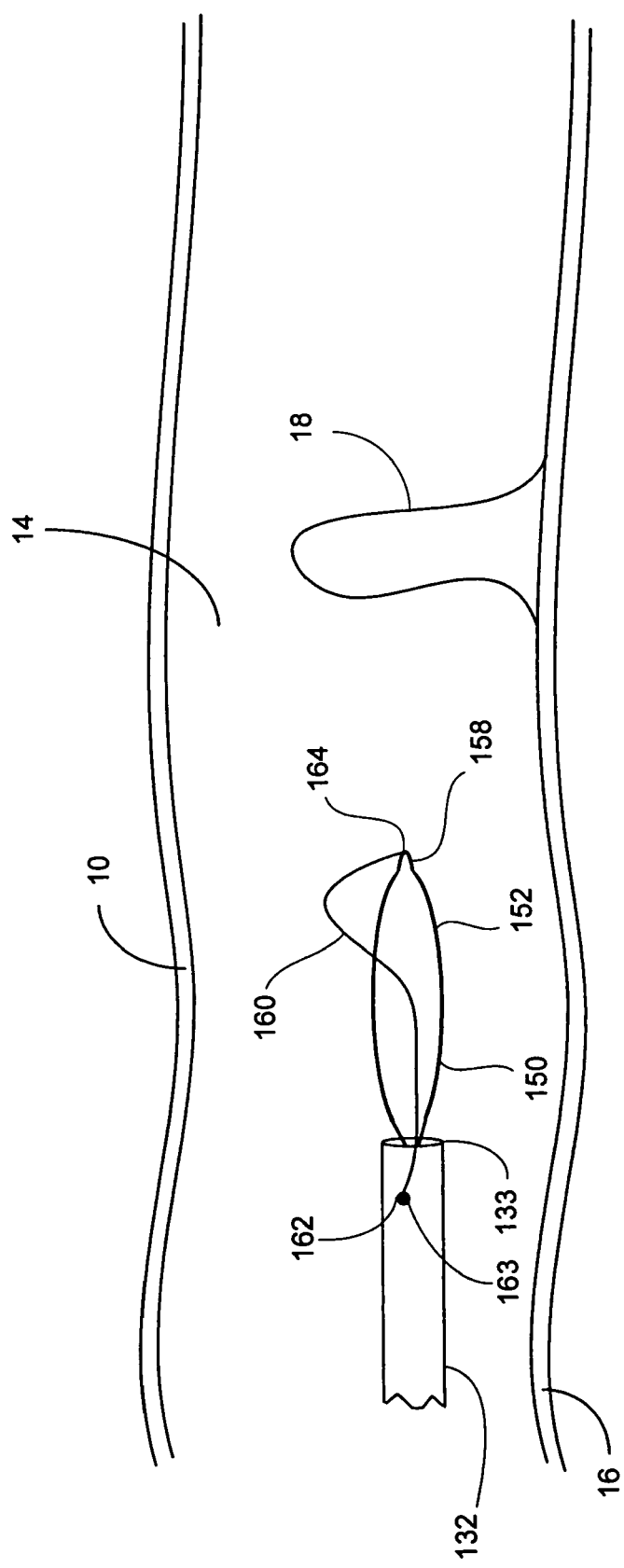
FIG. 7 is a perspective view of a snare loop of a surgical instrument according to the invention illustrating a step in a sequence of encircling a polyp with the snare loop.
Figure 8:
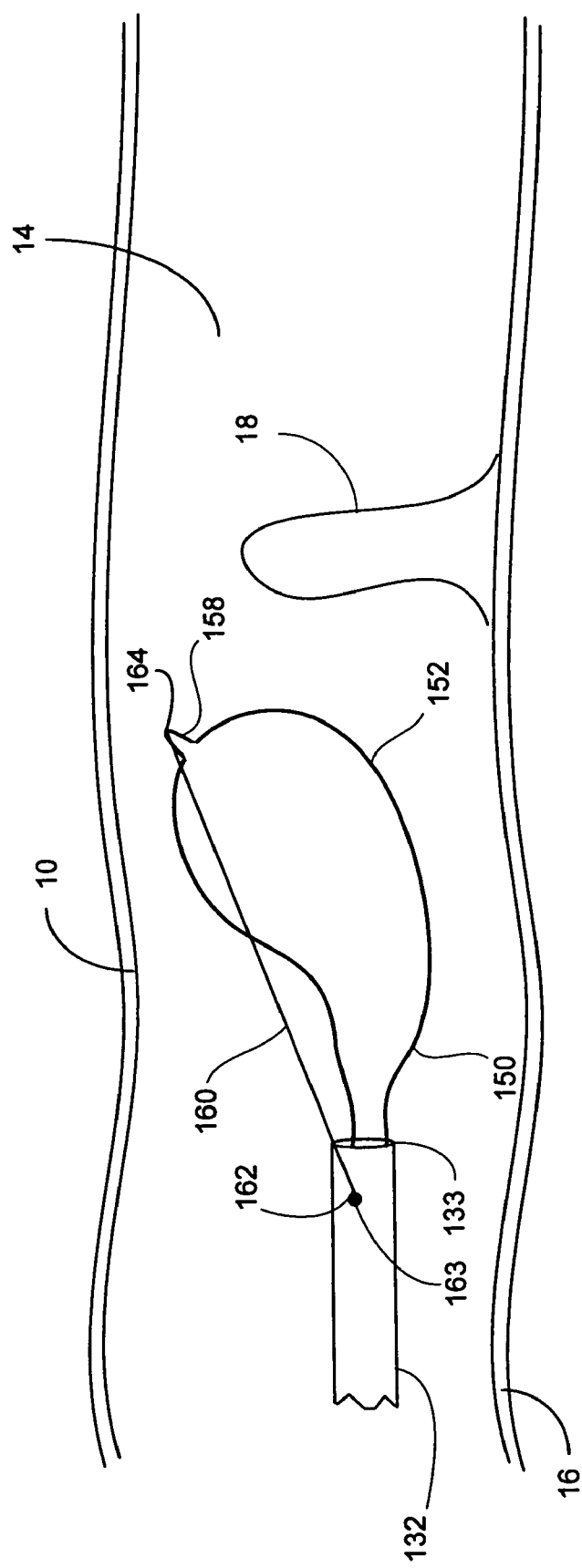
FIG. 8 is a perspective view of a snare loop of a surgical instrument according to the invention illustrating another step in a sequence of encircling a polyp with the snare loop.

FIGS. 7–10 illustrate a sequence by which the snare loop 150 can be used to encircle a polyp 18 attached to the lower tissue wall 16. Initially, the snare loop 150 is generally in its stowed position or, if deployed, is positioned near the distal tube end 133. At this point, the tether 160 is in a slack condition (i.e., is not under tension). As shown in FIG. 7, the snare loop 150 may be at a level where it cannot easily be positioned over the top of the polyp 18. This problem can occur as a result of the geometry of the cavity 14 and the stiffness of the tube 132. The tether 160, however, provides a way of deforming the snare loop 150 to overcome the problem. Further movement of the flexible cable 134 in the distal direction causes the snare loop to extend further from the distal tube end 133 until a critical length is reached where the tether 160 becomes taut. Moving the flexible cable 134 still further causes the snare loop 150 to deform as shown in FIG. 8. The movement of the flexible cable 134 may be accomplished using the control slide 122. As shown in FIG. 8, extending the snare loop 150 by moving the control slide 122 distally relative to the body 112 of the snare control module 110 creates a tensile force as the tether 160 remains the same length while the extended portion of the snare loop 150 and cable 134. This tensile force causes the snare loop 150 to deform so that the distal portion of the snare loop member 152 may be raised above the level of the polyp.

Figure 9:
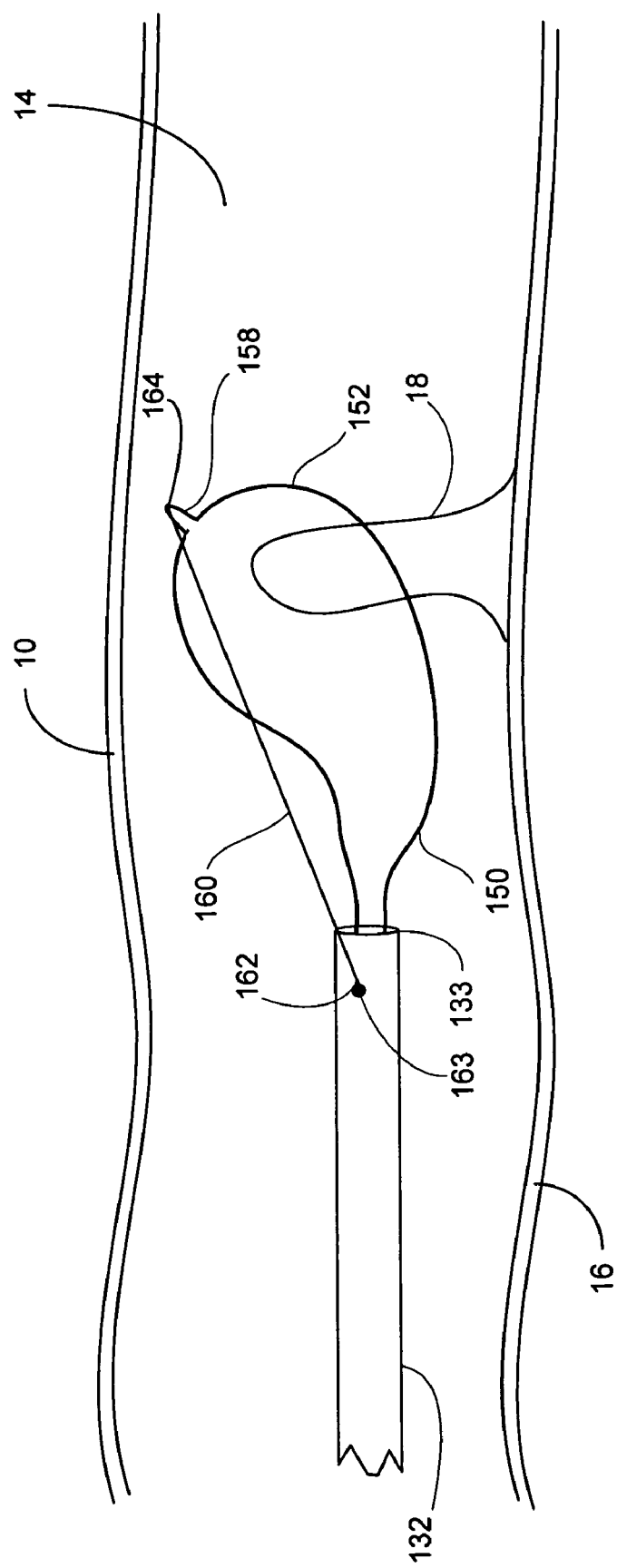
FIG. 9 is a perspective view of a snare loop of a surgical instrument according to the invention illustrating another step in a sequence of encircling a polyp with the snare loop.
Figure 10:
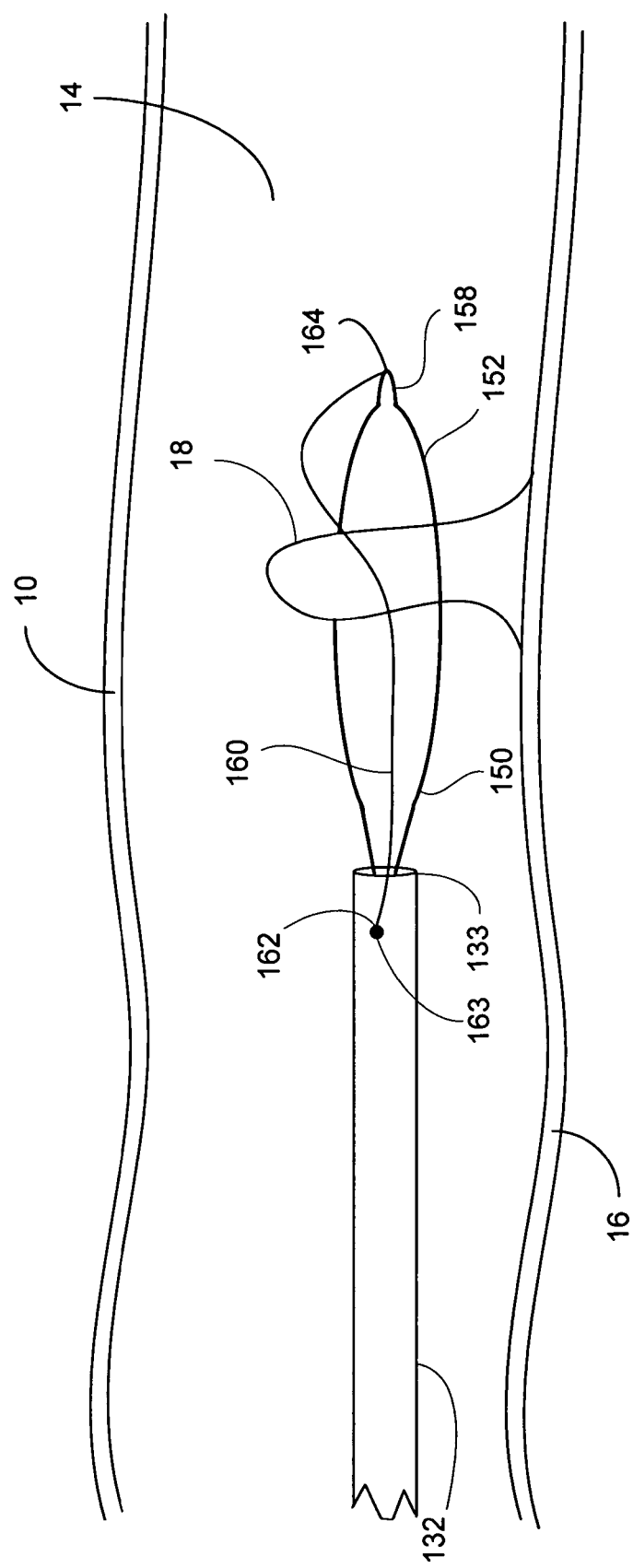
FIG. 10 is a perspective view of a snare loop of a surgical instrument according to the invention illustrating another step in a sequence of encircling a polyp with the snare loop.

When the snare loop 150 has been deformed into a desired deformed condition, the flexible tube 132 can then be translated further into the cavity 14 to position the snare loop 150 over the polyp 18 as shown in FIG. 9. The surgeon can then release the tension in the tether 160 by moving the flexible cable 134 proximally relative to the cable passageway 125. Retracting the cable 134 and the snare loop 150 releases the tension in the tether 160, which allows the snare loop 150 to resume its shape and encircle the polyp 18 as shown in FIG. 10. When releasing the tension in the tether 160, it may be necessary for the surgeon to simultaneously advance the flexible tube 132 slightly to assure that the snare loop 150 properly encircles the polyp. The snare loop 150 can then be cinched around the polyp 18 by further moving the flexible cable 134 proximally relative to the cable passageway 125. The snare loop 150 may be removed from the polyp 18 by reversing the above procedure.

Figure 11:
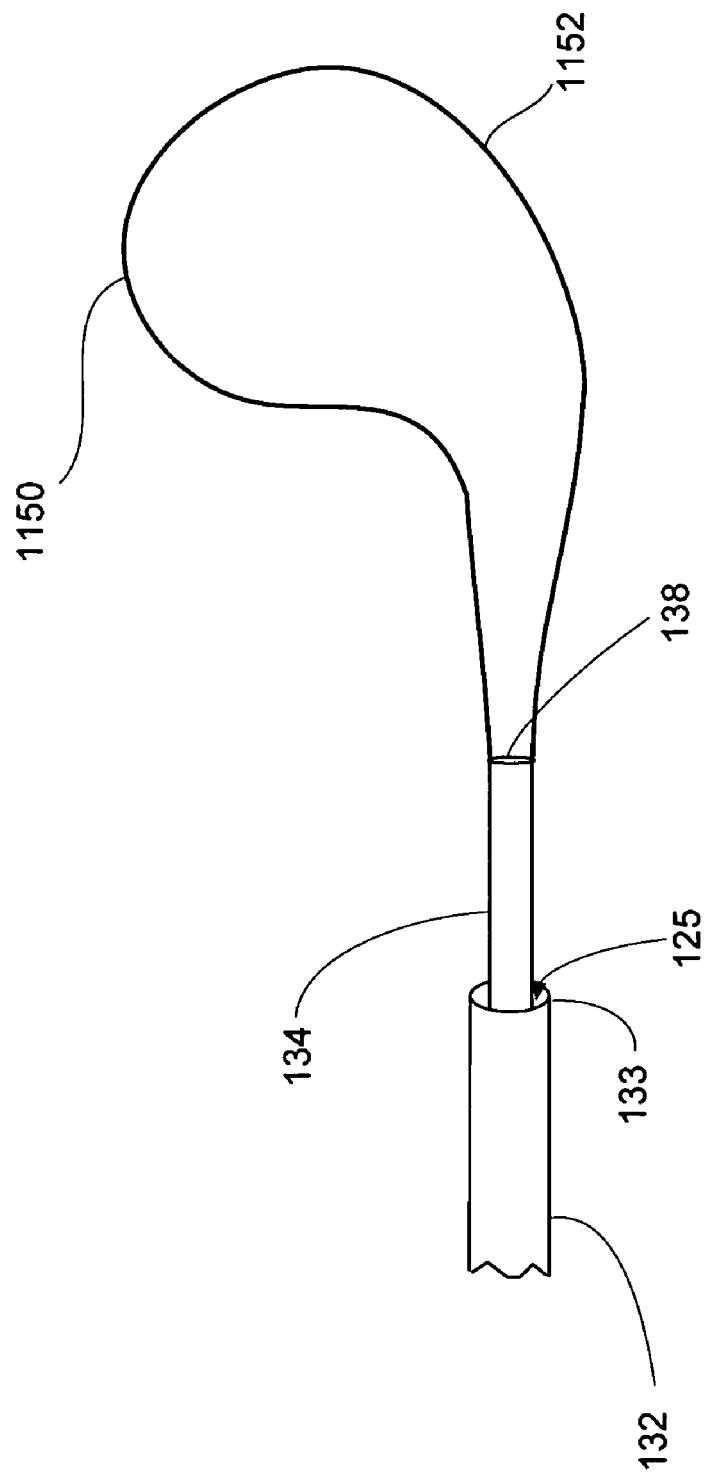
FIG. 11 is a perspective view of a snare loop of a surgical instrument according to an embodiment of the invention.

In some embodiments of the invention, the surgical instrument 100 may alternatively have a pre-deformed snare loop 1150 attached to the distal end 138 of the flexible cable 134, as shown in FIG. 11. Unlike the snare loop 150 of FIGS. 1–10, the pre-deformed snare loop 1150 of FIG. 11 is biased so as to adopt a three dimensional "deformed" condition when unconstrained. As a result, no tether is required. The snare loop 1150 of these embodiments is formed from a loop member 1152 comprising a memory retaining material that can be pre-formed to adopt a desired shape. Once so-formed, the loop member 1152 can be compressed so as to fit within a constraining space such as the cable passageway 125. When subsequently removed from the constraining space the loop member 1152 re-adopts the pre-formed three-dimensional shape. The memory retaining material may be any medical-grade material that is sufficiently resilient and will provide the desired capture shape. Such materials may include shap metal alloys such as nitinol.

Figure 12:
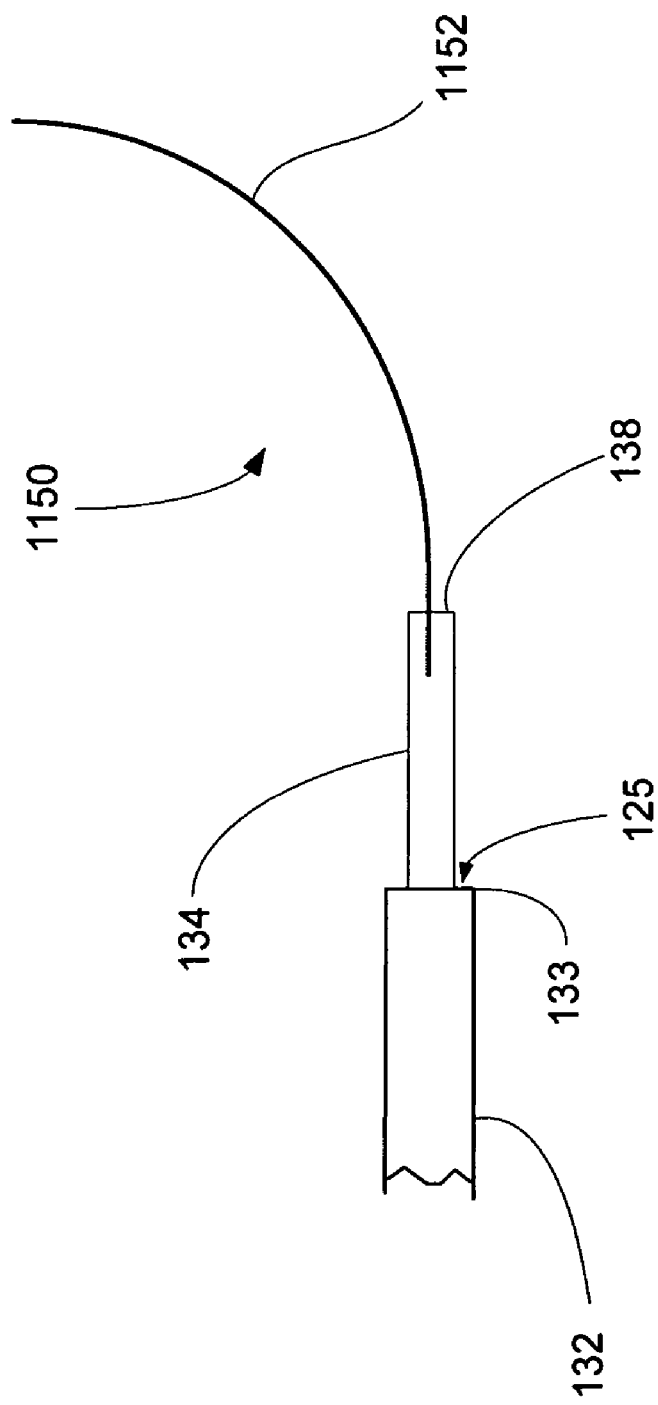
FIG. 12 is a side view of a the snare loop illustrated in FIG. 11.

Embodiments of the invention having the pre-deformed snare loop 1150 may be used in a substantially similar manner to the embodiments having the tethered snare loop 150. At the time of manufacture, the snare loop 1150 is deformed such that the fully deployed snare loop 1150 has a pre-determined three dimensional shape intended to facilitate capture of bodily tissue. This shape may be similar to that achieved with the tether of previous embodiments. For example, as shown in the side view depicted in FIG. 12, the loop member 1152 may be pre-formed to adopt a continuous curve as viewed in a vertical, longitudinal plane. This curve is oriented so that the loop member 1152 bends continuously away from an axis 139 centered on the flexible cable 134 at its distal end 138.

While the pre-deformed snare loop 1150 is in a stowed position within the cable passageway 125, the loop member 1152 presents a substantially linear shape as viewed in the vertical, longitudinal plane. However, when the flexible cable 134 is extended distally and the snare loop 1150 is deployed from the cable passageway 125, the loop member 1152 begins to "self-deform." Once completely unconstrained, the loop member 1152 returns to the desired pre-formed three dimensional shape. The instrument can then be used to capture tissue in substantially the same manner as described above. The pre-deformed loop 1150 is positioned adjacent the tissue so that retraction of the pre-deformed loop 1150 causes it to at least partially encircle the tissue. Further retraction causes the pre-deformed loop 1150 to be cinched around the tissue.

Figure 13:
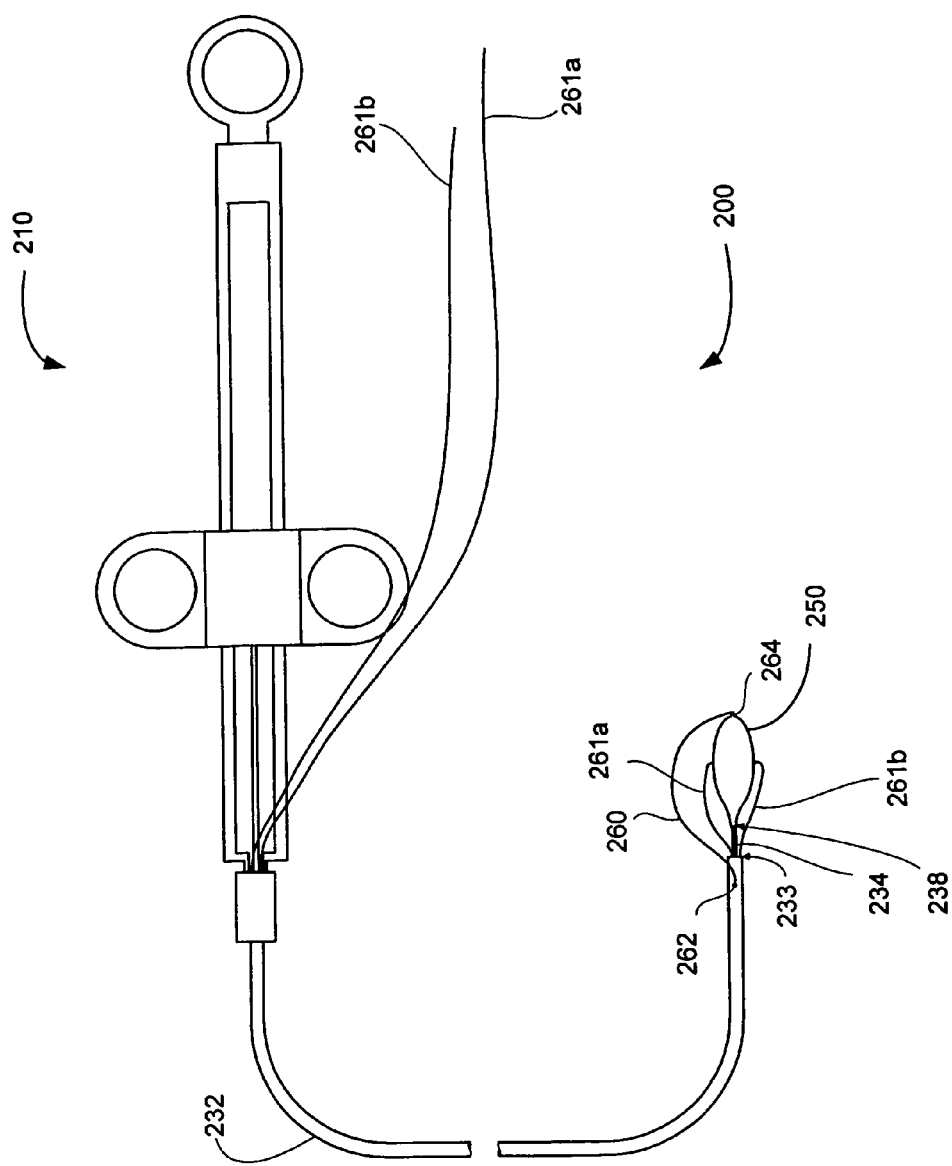
FIG. 13 is a partially sectioned view of a surgical instrument according to an embodiment of the invention.
Figure 14:
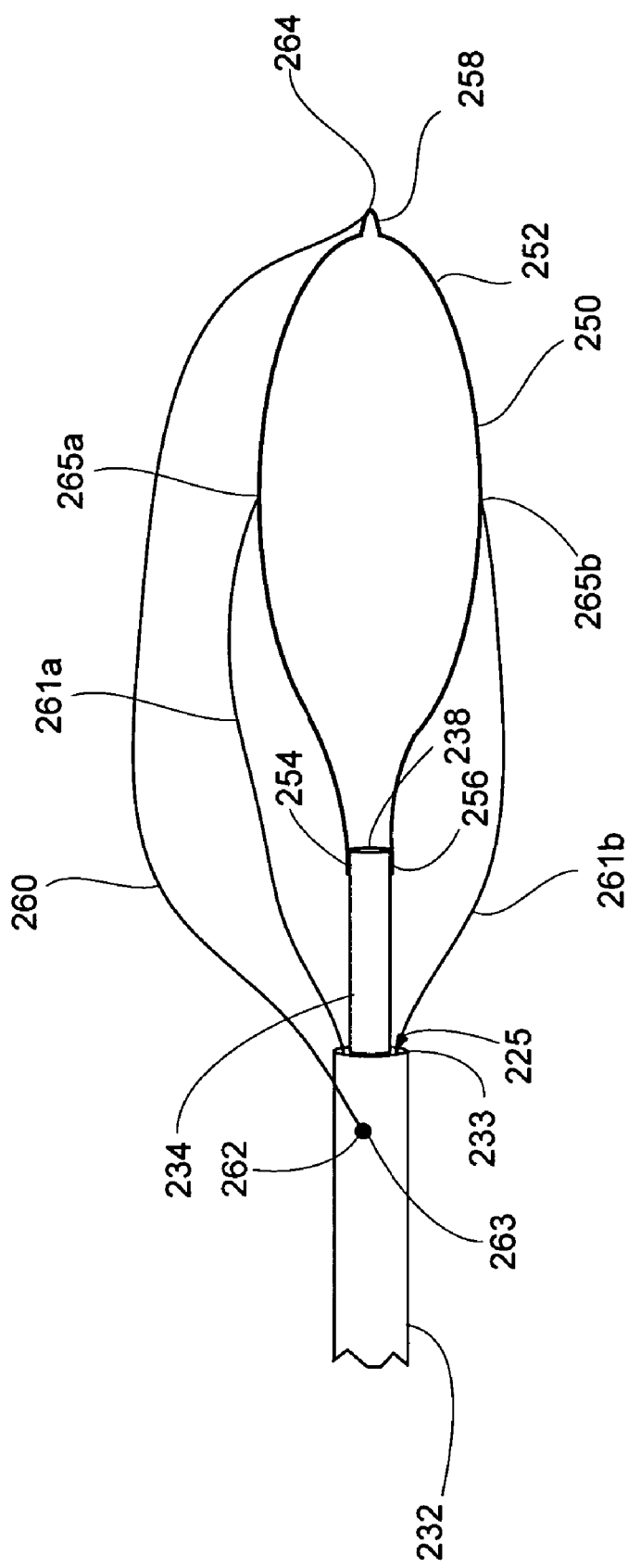
FIG. 14 is a perspective view of a snare loop of the surgical instrument illustrated in FIG. 13.

A surgical instrument 200 according to another embodiment of the invention is shown in FIGS. 13 and 14. The surgical instrument 200 may include a snare control module 210 that is used to control the deployment and retraction of a snare loop 250 from a flexible tube 232. The snare loop 250 is formed from a resilient loop member 252. The loop member 252 has first and second ends 254, 256 that are attached to a flexible cable 234 at its distal end 238. The materials and configuration of these features are similar to those of the previous embodiments.

As before, the flexible cable 234 is slidably disposed within a flexible tube 232. The flexible tube 232 has an inside diameter sized to accommodate the flexible cable 234 and the snare loop 250. In particular, the flexible tube 232 is sized so that the snare loop 250 can be easily retracted into the distal end 233 of the flexible tube 232 when the flexible cable 234 is moved proximally relative to the flexible tube 232 and extended out of and from the flexible tube 232 when the cable is moved distally relative to the flexible tube 232.

The surgical instrument 200 includes a fixed tether 260 and one or more manipulable tethers 261a, 261b as illustrated in FIGS. 13 and 14. The fixed tether 260 is similar to the fixed tether 160 of the surgical instrument 100 of FIGS. 1–10. The proximal end of the fixed tether 260 is attached to the flexible tube 232 at an attachment point 263. The distal end 264 of the fixed tether 260 is attached to the distal tip of the snare loop 250. The fixed tether 260 provides a similar automatic deformation of the snare loop 250 as before.

The manipulable tethers 261a, 261b provide the capability to manually maneuver snare loop 250 when the snare loop 250 has been deployed from the flexible tube 232. The distal ends 265a, 265b of the manipulable tethers 261a, 261b are each attached to the snare loop 250. As shown, the manipulable tethers 261a, 261b may be attached to opposite sides of the snare loop 250 so that the manipulable tethers 261a, 261b may be used as reins to steer the snare loop 250. Although two manipulable tethers are shown, it will be understood by those of ordinary skill in the art that any number of manipulable tethers may be used without departing from the scope and spirit of the invention.

The manipulable tethers 261a, 261b are slidably disposed through the cable passageway 225 of the flexible tube 232 along with the flexible cable 234. The flexible tube 232 and, in particular, the may be sized so that the flexible cable 234 and the manipulable tethers 261a, 261b can be moved substantially independently within the cable passageway 225. The manipulable tethers 261a, 261b extend out of the distal end 233 of the flexible tube 232 along side the flexible cable 234.

As shown in FIG. 13, the manipulable tethers 261a, 261b may be passed through the flexible tube 232 and through the connector 230 into the opening 217 between the frame members 214, 216. The proximal ends 263a, 263b of the manipulable tethers 261a, 261b thus may be extended out from the body 212 of the snare control module 210 and may be secured in any suitable fashion or may be left as free ends for a surgeon to manipulate and tie off as desired. It will be apparent that pulling one of the manipulable tethers 261a, 261b in the proximal direction, will tug on the portion of the snare loop 250 to which that tether is attached, thereby causing an additional deformation of the snare loop 250 that can be used to assist in positioning the snare loop 250 for capture of tissue.

The fixed tether 260 of the surgical instrument 200 operates in a manner similar to the tether 160 of the previous embodiments. The manipulable tethers 261a, 261b may be used to steer and deform the snare loop 250 from side to side either before or after the snare loop 250 is placed in its fully deformed condition. Accordingly, the fixed tether 260 and the manipulable tethers 261a, 261b may be used individually or in combination to maneuver the snare loop 250 as desired.

It will be understood that the manipulable tethers may also be used in an instrument configuration wherein the tethers are not disposed through the tube 232 but are instead separately passed out of the body cavity through the cannula.

Figure 15:
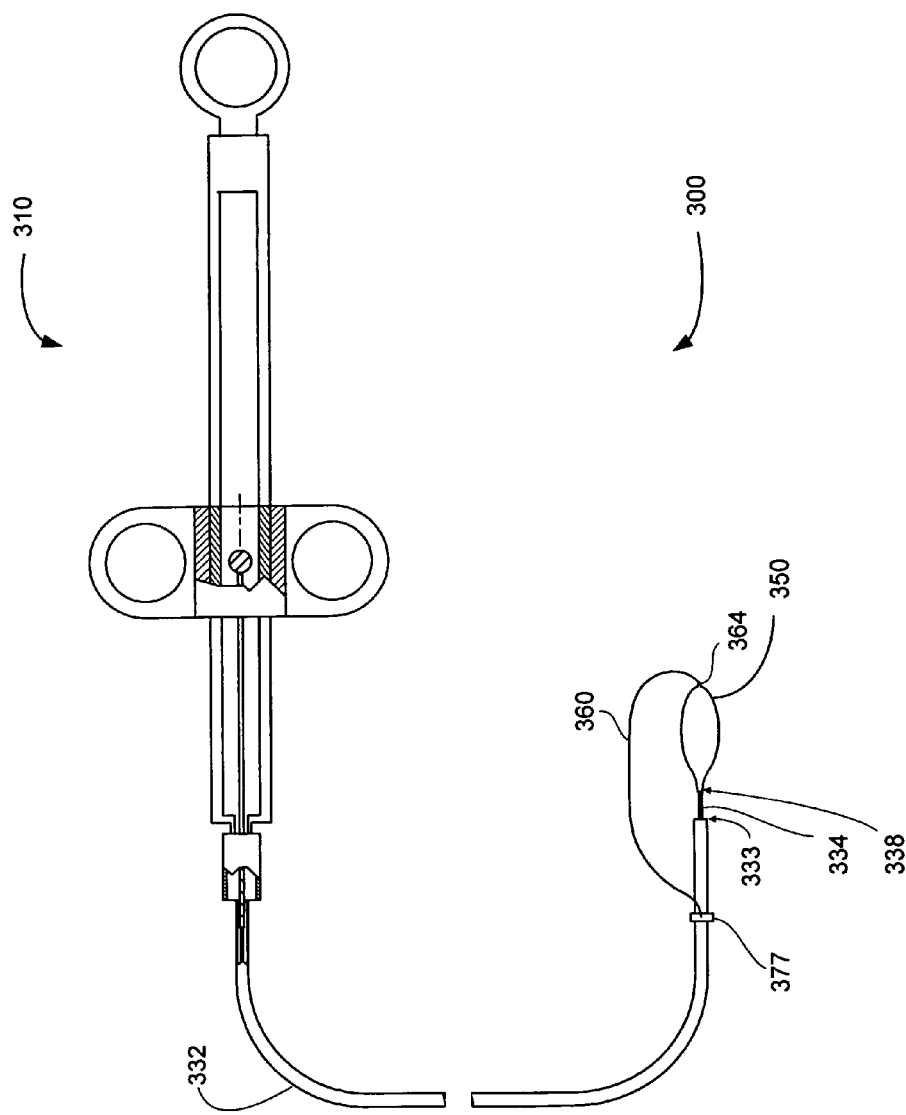
FIG. 15 is a partially sectioned view of a surgical instrument according to an embodiment of the invention.
Figure 16:
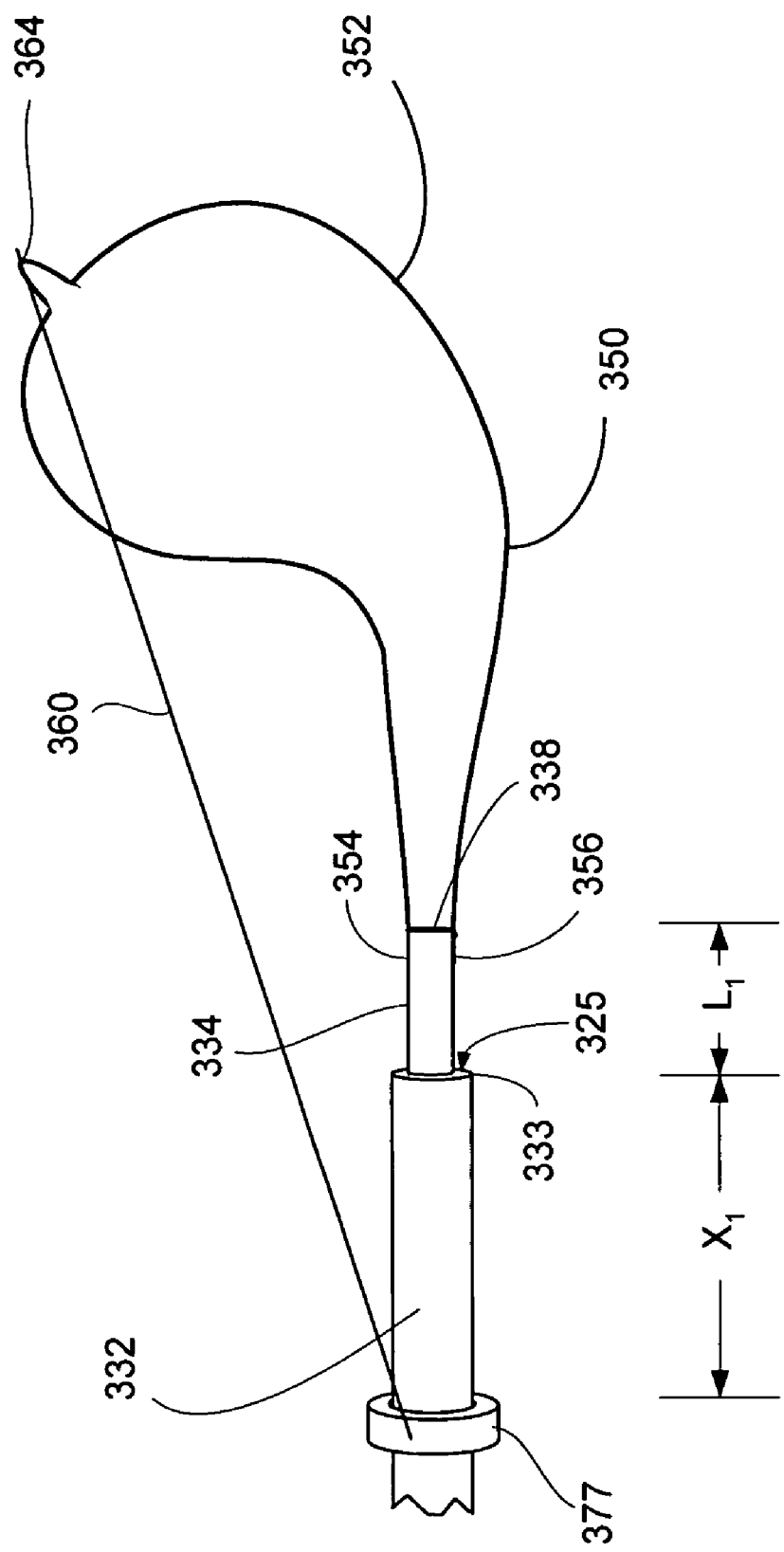
FIG. 16 is a perspective view of a snare loop of the surgical instrument illustrated in FIG. 15.
Figure 17:
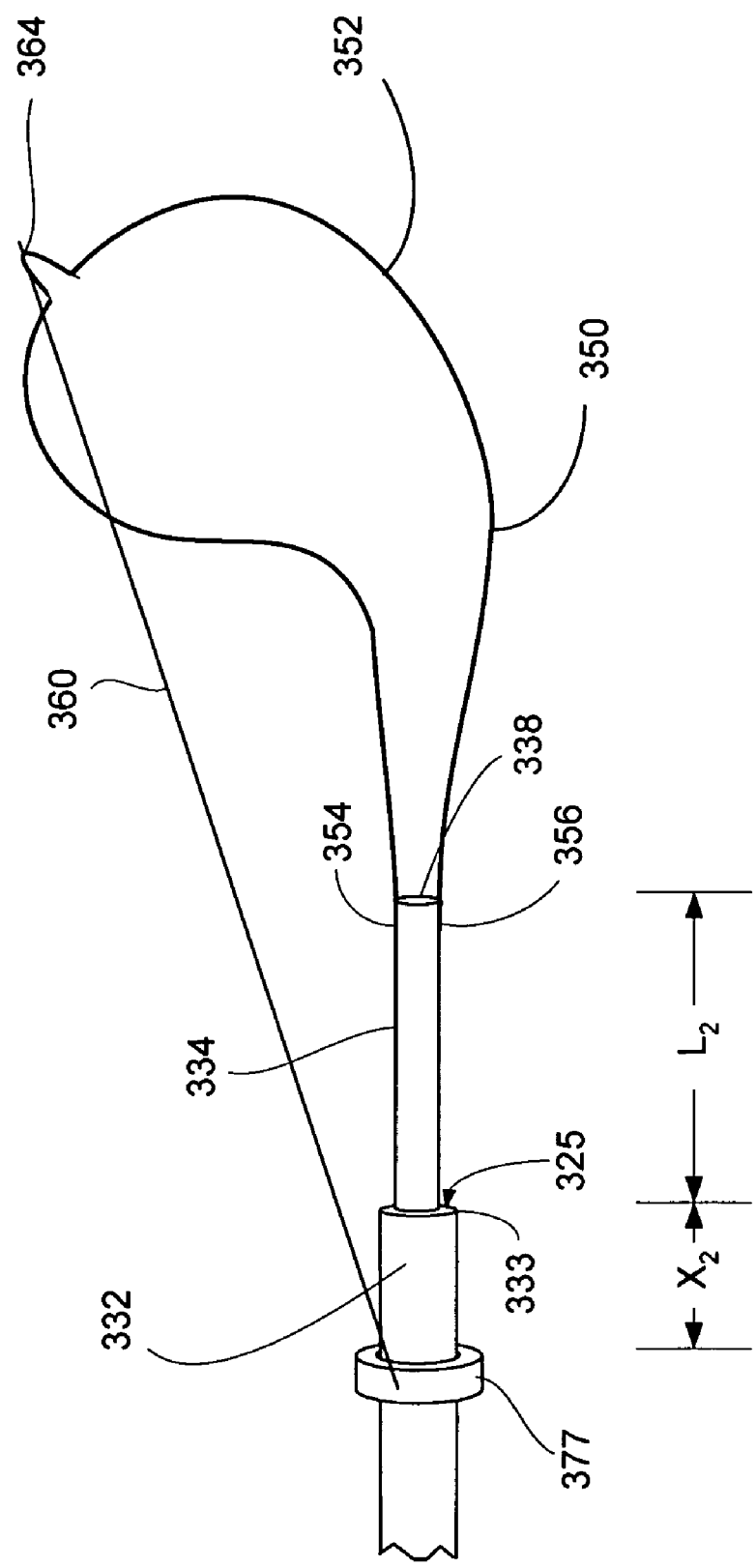
FIG. 17 is a perspective view of a snare loop of the surgical instrument illustrated in FIG. 15.

A surgical instrument 300 according to another embodiment of the invention is shown in FIGS. 15–17. The surgical instrument 300 may include a snare control module 310 that is used to control the deployment and retraction of a snare loop 350 from a flexible tube 332. The snare loop 350 is formed from a resilient loop member 352. The loop member 352 has first and second ends 354, 356 that are attached to a flexible cable 334 at its distal end 338. The materials and configuration of these features are similar to those of the previous embodiments.

As before, the flexible cable 334 is slidably disposed within a flexible tube 332. The flexible tube 332 has an inside diameter sized to accommodate the flexible cable 334 and the snare loop 350. In particular, the flexible tube 332 is sized so that the snare loop 350 can be easily retracted into the distal end 333 of the flexible tube 332 when the flexible cable 334 is moved proximally relative to the flexible tube 332 and extended out of and from the flexible tube 332 when the cable is moved distally relative to the flexible tube 332.

The surgical instrument 300 includes an adjustable tether 360 that provides automatic deformation of the snare loop 350 as in the previous embodiments. As in previous embodiments, the adjustable tether 360 has a distal tether end 362 attached to the loop member 352 and a proximal tether end 364 attached to the flexible tube 332. In this embodiment however, the proximal tether end 364 is attached to the flexible tube 332 by a tether adjustment member 377. The tether adjustment member 377 is formed as a collar that is slidably mounted to the flexible tube 332. The tether adjustment member 377 is constructed of a biologically inert material, such as the material used for the construction of the flexible tube 332. The tether adjustment member 377 is configured so that it can be selectively placed in various positions along the length of the flexible tube 332. This effectively changes the operative length of the adjustable tether 360, which, in turn, changes the point at which deformation begins when the snare loop 350 is deployed from the flexible tube 332. The tether adjustment member 377 thus allows the user to adjust the degree and timing by which the snare loop 350 is deformed as it is extended from the distal tube end 333.

The tether adjustment member 377 may include any suitable arrangement for selectively fixing its location such as, for example, a set screw (not shown).

FIGS. 16 and 17 illustrate the effect of the positioning of the tether adjustment member 377. As shown in FIG. 16, with the tether adjustment member 377 positioned a distance X1 from the distal tube end 333, extension of the loop member 350 a distance L1 from the distal tube end 333 provides a significant deformation of the loop member 350. As shown in FIG. 17, however, when the tether adjustment member 377 is positioned a distance X2 from the distal tube end 333 (X2 being less than X1), the snare loop 350 must be extended a greater distance L2 from the distal tube end 333 in order to achieve the same degree of deformation. Although the tether 360 is the same length in each case, the operative length of the tether 360 is changed, so that the snare loop 350 must be extended further before the tether 360 is placed in tension so as to deform the snare loop 350. This allows the surgeon to adjust the instrument for different applications prior to inserting the flexible tube 332 into the cannula.

It will be understood that the present invention may be applied to other forms of surgical instruments and snares. This includes snares with loops formed by a belt or wire having either or both ends passing out through a cannula. Such snares are typically cinched by applying tension to the free end (or ends) of the belt or wire. The tether of the present invention could easily be attached to the loops of such snares.

Other embodiments and uses of the invention will be apparent to those skilled in the art from consideration of the specification and practice of the invention disclosed herein. The specification and examples should be considered exemplary only. The scope of the invention is limited only by the claims appended hereto.

What is claimed is:

1. A surgical instrument for facilitating the capture of objects during surgery, the surgical instrument comprising:
    a flexible tube having a proximal tube end and a distal tube end, the flexible tube defining a cable passageway and being configured for insertion of at least a distal portion of the flexible tube into a body cavity of a patient;
    a flexible cable having a proximal cable end and a distal cable end, at least a portion of the flexible cable being slidably disposed in the cable passageway;
    a snare loop having a loop member attached to the distal cable end, the snare loop and the cable being adapted so that the snare loop can be selectively retracted within the cable passageway by sliding the flexible cable proximally relative to the cable passageway and so that at least a portion of the snare loop can be selectively extended from the distal tube end by sliding the flexible cable distally relative to the cable passageway, the snare loop having a longitudinal loop diameter and being adapted for selectively encircling and engaging at least a portion of an object in the body cavity; and
    a first tether having a proximal first tether end and a distal first tether end defining a tether length dimension, the distal first tether end being attached to the loop member and the proximal first tether end being connected to the flexible tube at an attachment point that is a predetermined distance from the distal tube end and wherein a ratio of the tether length dimension less the predetermined distance provides an operative tether length, a ratio of the operative tether length to the longitudinal loop diameter being in a range from about 0.3 to about 0.7.

2. A surgical instrument according to claim 1 wherein the proximal first tether end is connected to the flexible tube adjacent the distal tube end.

3. A surgical instrument according to claim 1 wherein the snare loop has a snare loop tip, the snare loop and the first tether being configured so that extending the snare loop tip from the cable passageway at least a predetermined distance causes the snare loop to deform in a first predetermined manner.

4. A surgical instrument according to claim 1 further comprising means for selectively controlling the extension of the snare loop from and the retraction of the snare loop into the cable passageway.

5. A surgical instrument according to claim 1 further comprising a snare control module having a body with a distal body end to which the flexible tube is connected and a proximal body end, and a control slide with a passage formed therein for slidable disposition of at least a portion of the body therethrough, the control slide being connected to the proximal end of the flexible cable by a control rod so that movement of the control slide toward the proximal body end causes proximal movement of the flexible cable relative to the cable passageway and movement of the control slide toward the distal body end causes distal movement of the flexible cable relative to the cable passageway.

6. A surgical instrument according to claim 1 wherein at least a portion of the first tether is connected to the flexible tube inside the cable passageway.

7. A surgical instrument according to claim 1 wherein the snare loop includes an electrically conductive cauterization wire.

* * * * *